(12) United States Patent
Kaneto et al.

(10) Patent No.: US 7,351,914 B2
(45) Date of Patent: Apr. 1, 2008

(54) FLEXIBLE PRINTED CIRCUIT BOARD FOR CATHETER, CATHETER USING SAME, AND PRODUCTION METHOD OF CATHETER

(75) Inventors: Masayuki Kaneto, Ibaraki (JP); Yasuhito Ohwaki, Ibaraki (JP); Tetsuya Ohsawa, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 11/405,587

(22) Filed: Apr. 18, 2006

(65) Prior Publication Data
US 2006/0244177 A1   Nov. 2, 2006

(30) Foreign Application Priority Data
Apr. 19, 2005   (JP) .............................. 2005-121493

(51) Int. Cl.
*H05K 1/00* (2006.01)
(52) U.S. Cl. .................... 174/254; 604/523; 604/96.01
(58) Field of Classification Search ................ 174/254, 174/256; 338/25
See application file for complete search history.

(56) References Cited

U.S. PATENT DOCUMENTS

| | | | |
|---|---|---|---|
| 4,435,614 A | 3/1984 | McAusland | |
| 5,795,299 A | 8/1998 | Eaton et al. | |
| 6,533,377 B2 * | 3/2003 | Su et al. | 347/1 |
| 2002/0049389 A1 * | 4/2002 | Abreu | 600/558 |
| 2002/0101461 A1 * | 8/2002 | Su et al. | 347/1 |
| 2002/0135454 A1 * | 9/2002 | Ichida et al. | 338/25 |
| 2002/0136547 A1 * | 9/2002 | Nomura et al. | 396/72 |
| 2003/0221861 A1 | 12/2003 | Dupriest | |
| 2004/0118595 A1 | 6/2004 | Flammer et al. | |

FOREIGN PATENT DOCUMENTS

EP   1 671 669   6/2006

* cited by examiner

Primary Examiner—Randy W. Gibson
Assistant Examiner—Abiy Getachew
(74) Attorney, Agent, or Firm—Wenderoth, Lind & Ponack, L.L.P.

(57) ABSTRACT

The present invention provides a flexible printed circuit board having a band-like meandering pattern as a whole, which includes multiple linear parts configured about parallel to each other and a folding margin connected to one end in a longitudinal direction of two adjacent linear parts of the multiple linear parts, and which can turn into a single linear product having a total length of not less than 300 mm when the folding margin is double-folded at about a center thereof, and, at the folding margin, either of the two linear parts connected to the folding margin is folded back in a direction opposite by 180 degrees. As a result, a flexible printed circuit board for a catheter, which is sufficiently elongate for use as a signal line of a catheter, can be produced using a general-purpose production apparatus.

19 Claims, 12 Drawing Sheets

FLEXIBLE PRINTED CIRCUIT BOARD FOR CATHETER, CATHETER USING SAME, AND PRODUCTION METHOD OF CATHETER

TECHNICAL FIELD OF THE INVENTION

The present invention relates to a flexible printed circuit board for a catheter, a catheter using the circuit board, and a production method of the catheter. More particularly, the flexible printed circuit board for a catheter is long but easy to manufacture, and improves a degree of freedom of deformation and movement in a tube.

BACKGROUND OF THE INVENTION

Conventionally, various tests and treatments are performed based on electrical signals transmitted by electronic components, such as a heat element, a pressure sensor, a temperature measurement thermistor and the like, set in an anterior end or an intermediate part of a tube of a catheter inserted into a body of a patient. Such an electronic component-loaded catheter is described, for example, in JP-A-11-56794 and JP-A-2001-170013.

The aforementioned "anterior end of a tube" means an end of a head of a catheter (tube) in a length direction, which is to be inserted into the body of a patient, and the "anterior end of a tube" in the following description in the present specification means an end of the head of a catheter (tube) in the length direction when inserted into the body of a patient, and the "posterior end of a tube" means another end of the tube, which is an opposite side from the head, in the length direction.

In the above-mentioned catheter comprising an electronic component in a tube, an electrical signal sent by an electronic component in the anterior end or an intermediate part of a tube inserted in the body of a patient is processed by a measuring apparatus connected to the posterior end of the tube outside the body of the patient. When operation of the aforementioned electronic component is to be controlled, it is remotely controlled by a control device connected to the posterior end of a tube outside the body of the patient. Therefore, a signal line to transmit an electrical signal between the electronic component and a measuring apparatus, a control device and the like needs to be installed in a tube of an electronic component-loaded catheter. As such signal line, signal cables such as a flat cable and the like have been conventionally used, as in the catheters described in the aforementioned JP-A-11-56794 and JP-A-2001-170013. Recently, however, for higher functions of electronic components to be set in a tube, this kind of catheter is required to contain an increased number of signal lines. When a number of signal cables is increased to contain many signal lines, a tube containing the signal cables needs to be made thicker. As a result, problems of lower operability of a catheter in a body of a patient, increased pain felt by the patient during operation of the catheter and possible damage in the body of the patient occur. Since a mounting site of an electronic component is limited to a specific area at a tip of a signal cable, a number of electronic components to be mounted is limited. In addition, since a position of electronic components to be mounted is limited to the tip of a signal cable, a place where the electronic components operate as well as their functions are problematically limited.

Therefore, the present inventors have considered using a flexible printed circuit board as a signal line to be installed in a tube. To be specific, since a flexible printed circuit board can form an ultrafine high density wiring, when it is used as a signal line to be installed in a tube, a number of signal lines can be increased without greatly increasing a thickness of the tube. Since a terminal mounting an electronic component can be formed at a given position in a flexible printed circuit board, moreover, positions and a number of electronic components to be installed can be easily designed.

When a flexible printed circuit board is inserted in a tube for use as a signal line, however, since the flexible printed circuit board needs to be formed in a long, linear pattern, a production cost of a product showing highly uniform properties becomes high. To be precise, in most cases, a photolithography step is included in production of a flexible printed circuit board, which uses a general-purpose exposing apparatus having an exposure area of generally about a 250 mm×250 mm square. When one linear flexible printed circuit board having a total length of not less than 300 mm is to be produced, it needs to be exposed to light multiple times in multiple steps, or an exposure mask having a considerably extended length needs to be prepared, or an exposure surface needs to have a considerably large linear length, which causes a high cost. Moreover, exposure at multiple times in multiple steps may result in occurrence of disconnection between exposed areas.

In addition, while a flexible printed circuit board is advantageous for decreasing a diameter of a catheter as compared to wire cables, a degree of freedom of movement in a tube is generally smaller than wire cables, and operability (deformability) of a catheter using a flexible printed circuit board as a signal line is not entirely satisfactory.

In view of the above-mentioned situation, a problem to be solved by the present invention is provision of a flexible printed circuit board for a catheter, which is sufficiently elongate for use as a signal line of a catheter, can be produced using a general-purpose production apparatus, and can improve a degree of freedom of movement in a tube, a catheter comprising the flexible printed circuit board and a production method thereof.

SUMMARY OF THE INVENTION

The present invention solves the above-mentioned problem by the following constitutions.

(1) A flexible printed circuit board for a catheter, which is formed in a single non-linear band-like pattern having a folding margin at a predetermined position, wherein the flexible printed circuit board can turn into a single linear product when folded at the folding margin.

(2) The flexible printed circuit board of the above-mentioned (1), wherein the single linear product has a total length of not less than 300 mm.

(3) The flexible printed circuit board of the above-mentioned (1),
which has a band-like meander pattern as a whole,
which comprises multiple linear parts configured about parallel to each other and a folding margin connected to one end in a longitudinal direction of two adjacent linear parts of the multiple linear parts, and
which can turn into a single linear product when the folding margin is double-folded such that a folding line parallel to an axis of the linear parts is formed in about a center thereof, and, at the folding margin, either of the two linear parts connected to the folding margin is folded back in a direction opposite by 180 degrees.

(4) The flexible printed circuit board of the above-mentioned (3), wherein the single linear product has a total length of not less than 300 mm.

(5) The flexible printed circuit board of the above-mentioned (1), wherein a size of the band-like pattern as a whole before folding is within a 250 mm×250 mm square area.

(6) The flexible printed circuit board of the above-mentioned (1), which further comprises a metal support plate disposed in an area other than a folding line.

(7) The flexible printed circuit board of the above-mentioned (1), wherein two opposite substrate surfaces after folding at a folding margin are adhered via an adhesive layer.

(8) A catheter comprising the flexible printed circuit board of the above-mentioned (1) in the form of a single linear product inserted in a tube.

(9) A production method of a catheter, which comprises step 1: folding the flexible printed circuit board of the above-mentioned (1) at a folding margin to provide a single linear product, and step 2: inserting this resulting flexible printed circuit board into a tube.

(10) The production method of the above-mentioned (9), wherein step (1) comprises adhering, via an adhesive layer, two opposite substrate surfaces after folding at the folding margin.

(11) A production method of a catheter, which comprises step 1: folding a flexible printed circuit board of the following (I) at a folding margin to provide a single linear product, and step 2: inserting this resulting flexible printed circuit board into a tube, wherein, in step 1, the folding margin is double-folded such that a folding line parallel to an axis of linear parts is formed in about a center thereof, and, at the folding margin, either of two linear parts connected to the folding margin is folded back in a direction opposite by 180 degrees, so as to convert the circuit board into a single linear product;

(I) a flexible printed circuit board for a catheter, which is formed in a single non-linear band-like pattern having a folding margin at a predetermined position, wherein the flexible printed circuit board can turn into a single linear product when folded at the folding margin, which has a band-like meander pattern as a whole, which comprises multiple linear parts configured about parallel to each other and a folding margin connected to one end in a longitudinal direction of two adjacent linear parts of the multiple linear parts, and which can turn into a single linear product when the folding margin is double-folded such that a folding line parallel to an axis of the linear parts is formed in about a center thereof, and, at the folding margin, either of two linear parts connected to the folding margin is folded back in a direction opposite by 180 degrees.

In the Figures, each reference number designates the following. 1: linear part, 2: folding margin, 10: base insulating layer, 11: wiring pattern, 12: cover insulating layer, 100: flexible printed circuit board (FPC).

DETAILED DESCRIPTION OF THE PREFERRED EMBODIMENTS

While a flexible printed circuit board for a catheter of the present invention is originally a non-linear product, it can turn into a single linear product by folding at folding margin(s).

Thus, it is possible to produce a non-linear circuit board product having a size of an entire band-like pattern before folding within, for example, a 250 mm×250 mm square area. Then, the circuit board can turn into a linear product having a total length of not less than 300 mm by folding at folding margin(s).

In a photolithography step during production, therefore, it is not necessary to conduct exposure multiple times in plural steps or use a light exposure mask having a considerably extended linear part. Instead, the light exposure can be applied all at once using a general-purpose exposing apparatus, by which a production cost can be suppressed. In addition, a flexible printed circuit board for a catheter having highly uniform properties can be realized.

In a flexible printed circuit board formed into a single linear product by folding at folding margin(s), a folded part absorbs stress applied to linear parts before and after the folded part, and therefore, a degree of freedom of movement in a tube becomes high. Therefore, when the flexible printed circuit board of the present invention is used as a signal wiring, a catheter having a small diameter and superior operability (deformability) can be realized.

The present invention is explained in more detail in the following by referring to the Figures.

Figure 1:
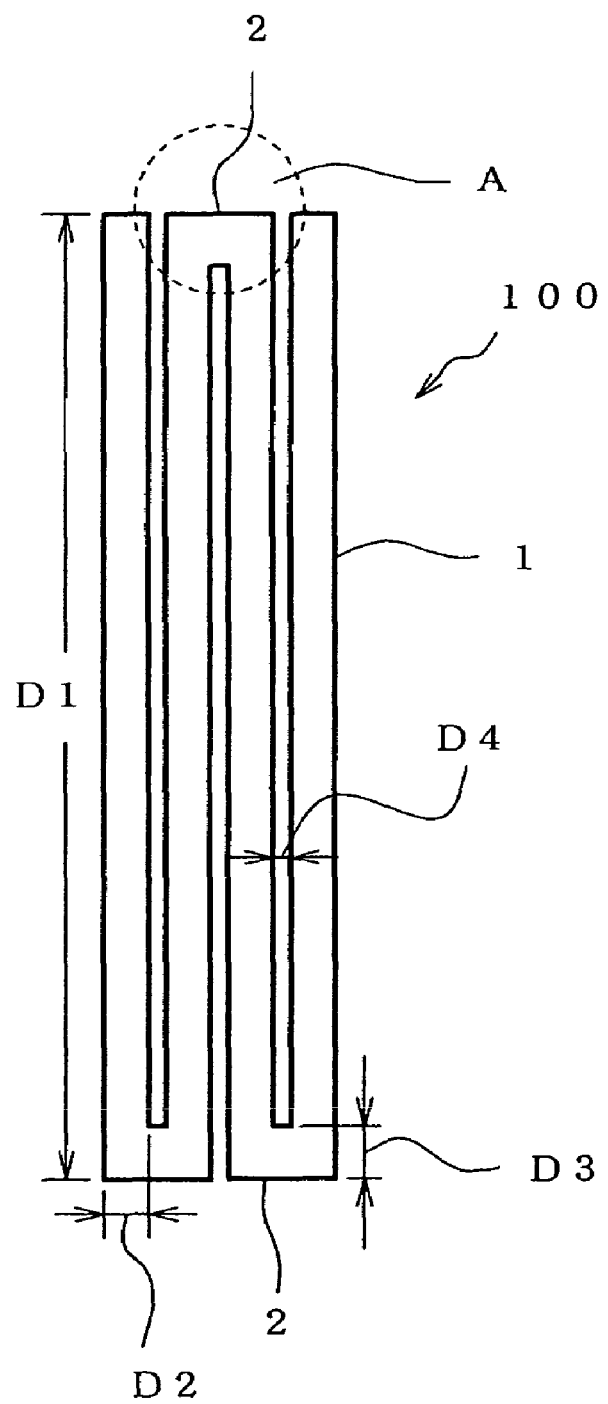
FIG. 1 is a simplified plan view of a flexible printed circuit board for a catheter of one embodiment of the present invention.
Figure 2:
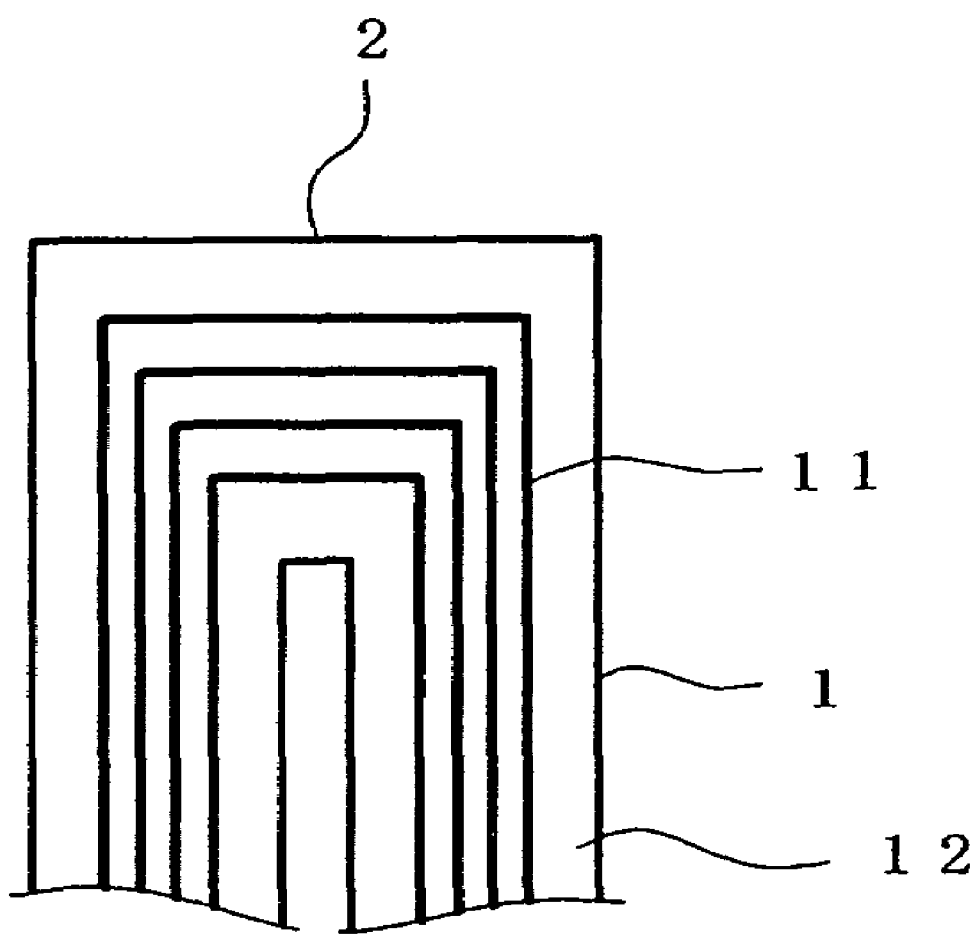
FIG. 2 is an enlarged view of area A encircled with a dotted line in FIG. 1.

FIG. 1 is a plan view of a flexible printed circuit board for a catheter of one embodiment of the present invention, and FIG. 2 is an enlarged view of a main part (area A encircled with a dotted line) in FIG. 1.

As shown in this embodiment of flexible printed circuit board (hereinafter to be also abbreviated as "FPC") 100, the flexible printed circuit board for a catheter of the present invention has been formed in a non-linear, elongate band-like pattern having a total length of generally not less than 300 mm. In FIG. 2, 11 is a wiring pattern and 12 is a cover insulating layer. The wiring pattern 11 is formed on a base insulating layer not shown, and the cover insulating layer 12 is formed to cover the wiring pattern 11.

In the embodiment, the flexible printed circuit board 100 comprises multiple linear parts 1 configured about parallel to each other, and folding margins 2 connected to one end of end portions in a longitudinal direction of each set of two adjacent linear parts 1 of the multiple linear parts, and has a band-like meander pattern as a whole. The flexible printed circuit board 100 turns into a single linear product upon predetermined folding at individual folding margins 2.

Figure 3A:
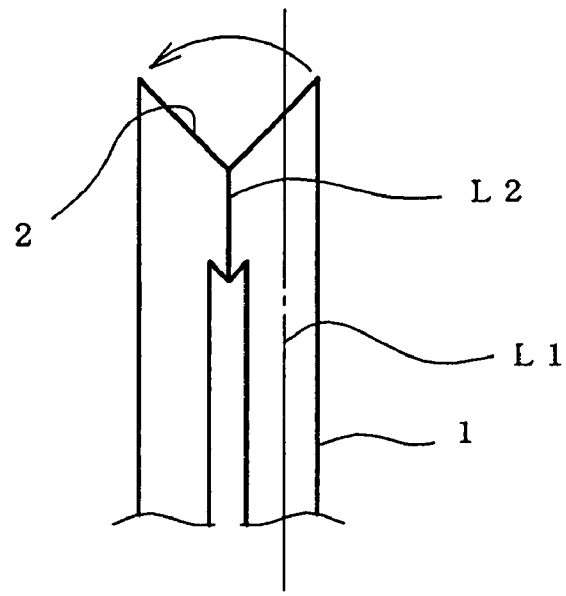
FIGS. 3(a)-3(c) show simplified views of how the flexible printed circuit board for a catheter of the present invention is sequentially folded to form a linear product.
Figure 3B:
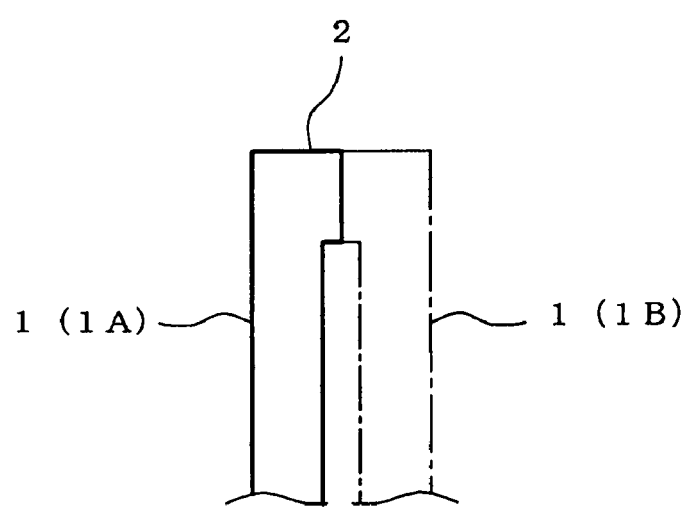
Figure 3C:
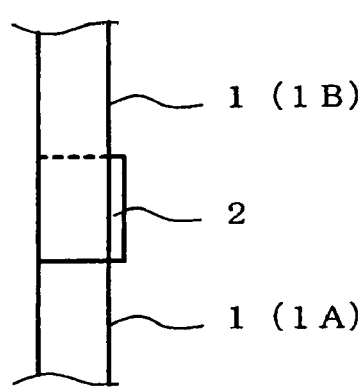
Figure 4:
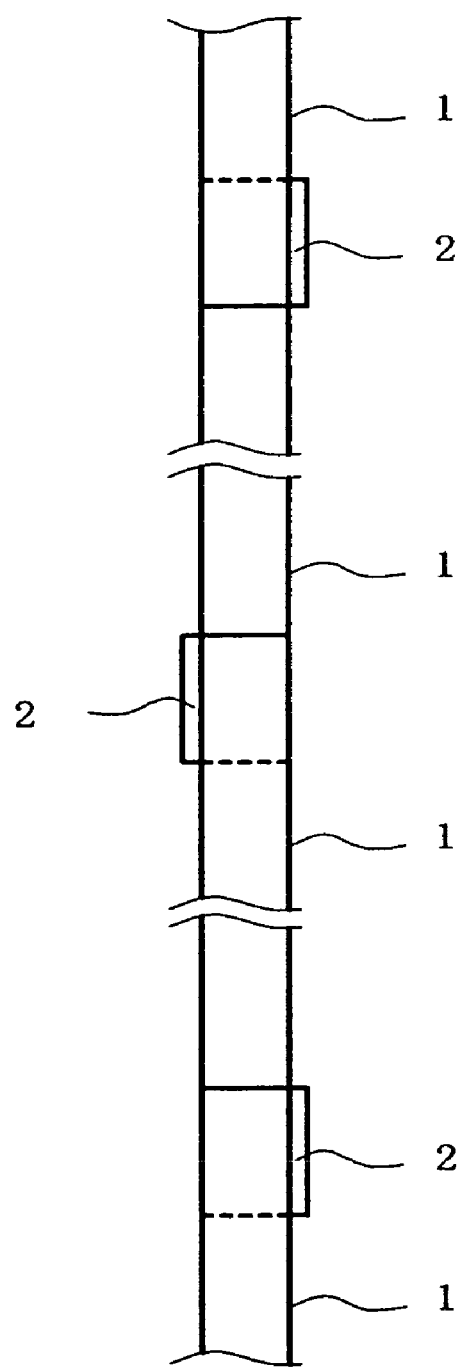
FIG. 4 is a simplified view of a linear product obtained by folding the flexible printed circuit board for a catheter as shown in FIG. 1 at a folding margin into one linear product.

To be specific, folding margin 2 is, as shown in FIG. 3(a), double-folded such that a folding line L2 parallel to axis L1 of linear part 1 is formed at about a center thereof as shown in FIG. 3(b), and, as shown in FIG. 3(c), either of two linear parts 1 (1A, 1B) connected to the folding margin 2 is folded back in a direction opposite by 180 degrees. This step is performed at individual folding margins 2 to provide a single linear product having a total length of not less than 300 mm (FIG. 4).

As mentioned above, the inventive FPC for a catheter is, as shown in FPC 100 of the above-mentioned embodiment, has a single non-linear band-like pattern before folding at folding margin(s) 2, and can change into a single linear product having a total length of not less than 300 mm by folding at folding margins 2 formed at predetermined positions. In addition to this constitution, the band-like pattern in its entirety before folding is configured to a size within a square area of 250 mm×250 mm. As a result, during a photolithography step for production, it is not necessary to conduct exposure multiple times in plural steps or use a light exposure mask having a considerably extended linear part. Instead, the light exposure can be applied all at once using a general-purpose exposing apparatus. Therefore, a product having highly uniform properties can be obtained free of high production costs.

When FPC is a single linear product having a total length of not less than 300 mm by predetermined folding at each folding margin 2, a folded part in the folding margin 2 absorbs stress applied to linear parts before and after the folded part, and therefore, a degree of freedom of movement in a tube becomes high. Therefore, when the FPC of the present invention is used as a signal wiring to be connected to an electronic component, a catheter having superior operability can be realized.

The "non-linear band-like pattern" of the inventive FPC for a catheter before folding at folding margin(s) means a pattern comprising combinations of multiple linear parts and bending parts to be folding margins, so as to avoid an FPC elongate in one direction alone.

This pattern may be other than the meander pattern such as FPC 100 in the above-mentioned embodiment, which is exemplified by an eddy or volute pattern and the like. Since a manner of folding at folding margins to produce a single linear product can be simplified, the meander pattern of FPC 100 in the above-mentioned embodiment is preferable.

Furthermore, the "single linear product after folding at folding margin(s)" means that, in a plan view, the FPC as a whole generally appears to be a single linear product after folding at folding margin(s), and a structure where an axis of the multiple linear parts are aligned in one straight line with high precision is not meant in this context.

When the inventive FPC for a catheter is to be formed into an FPC having a band-like meander pattern as a whole and comprising, as in FPC 100 of the above-mentioned embodiment, multiple linear parts 1 configured about parallel to each other and a folding margin 2 connected to one end in a longitudinal direction of each set of two adjacent linear parts 1 of the multiple linear parts, a total number of linear parts 1 may be appropriately selected from a range of 2-10 depending on a size (length) and structure of a catheter to be produced, while the FPC of FIG. 1 comprises four linear parts 1.

Length D1 of the linear part 1 (width in the axial direction) is generally selected from a range of 100-400 mm, and width D2 (width in a direction perpendicular to the axial direction) is selected from a range of 0.1-3 mm.

A total number of the folding margins 2 is generally selected from a range of 1-9 since the total number of the linear parts 1 is 2-10, and width D3 in a direction perpendicular to an axis of the folding margin 2 is generally selected from a range of 0.3-10 mm.

Clearance D4 between two adjacent linear parts 1 is generally within a range of 0.02-5 mm.

Figure 5A:
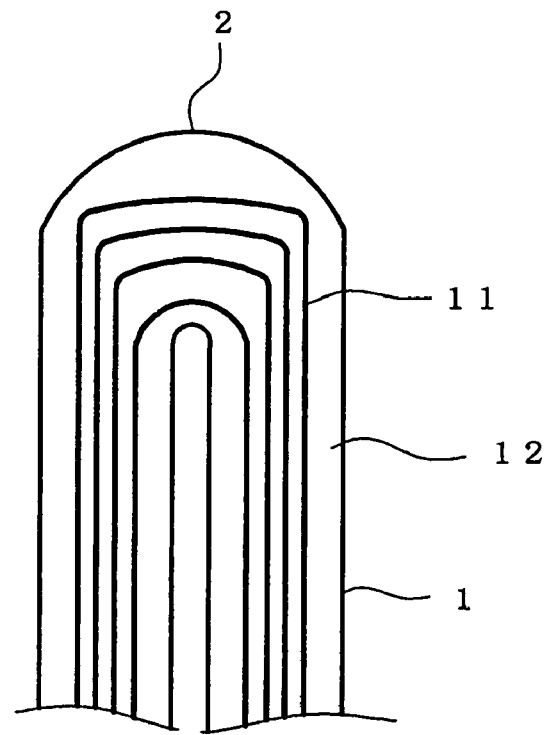
FIGS. 5(a) and 5(b) show deformation examples of the folding margin of the flexible printed circuit board for a catheter of the present invention.
Figure 5B:
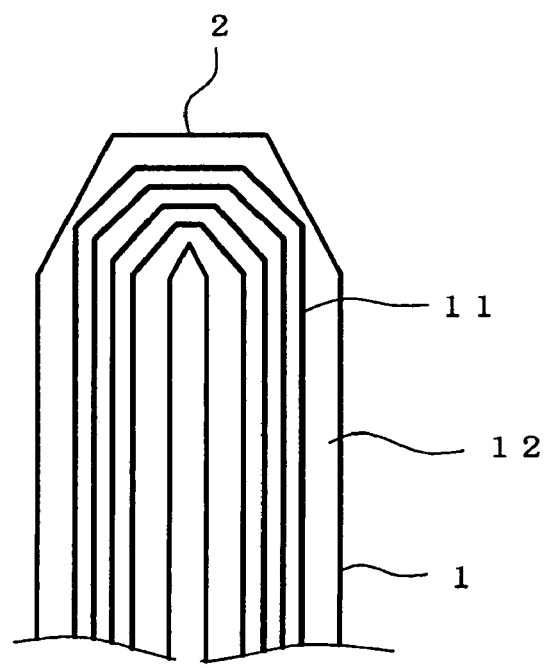

In the inventive FPC for a catheter, the "linear" of the linear parts 1 means that the axis is linear, and an outer line of linear part 1 may not be linear. In addition, a shape of the folding margin 2 is not particularly limited. For example, a rectangular shape (square shape) as shown in FIG. 2, a semicircular shape and a mixture as in FIG. 5(a), a trapezoidal shape as in FIG. 5(b) and the like can be mentioned.

When the folding margin 2 is of such a semicircular type or a trapezoidal type, an area of the folded part resulting from folding becomes smaller than that of a square type. In an embodiment of such a folding margin, a possibility of the folding margin 2 extending from an outer shape of a single linear FPC is preferably small, even if the linear parts 1 (axis thereof) before and after the folding margin fail to have a preferable shape where they are aligned in one straight line.

While a total length of the FPC of the present invention when it is a linear product is appropriately determined according to size (length) and structure of a catheter to be produced, it is generally within a range of not less than 300 mm and not more than 2500 mm.

Figure 6:
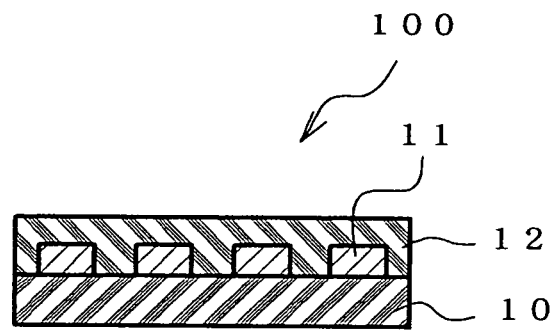
FIG. 6 is a sectional view of the flexible printed circuit board for a catheter shown in FIG. 1.

FIG. 6 is a sectional view of FPC 100 of the aforementioned one embodiment along a plane perpendicular to an axis of the wiring pattern. As shown in FIG. 6, the FPC of the present invention has a laminate structure wherein a base insulating layer 10, wiring pattern 11 and cover insulating layer 12 are laminated in this order, and is basically the same as that of the conventional FPC. For material of the base insulating layer 10, wiring pattern 11 and cover insulating layer 12, known materials conventionally used for FPC can be employed.

As the material of the base insulating layer 10, for example, polyimide resin, polyester resin, epoxy resin, urethane resin, polystyrene resin, polyethylene resin, polyamide resin, acrylonitrile-butadiene-styrene (ABS) copolymer resin, polycarbonate resin, silicone resin, fluorine resin and the like can be mentioned. Of these, polyimide resin is preferable from aspects of heat resistance, size stability, chemical resistance and the like. A thickness of the base insulating layer 10 is preferably about 5-100 μm, and more preferably about 8-30 μm, from aspects of flexibility and electrical insulation.

As the material of the wiring pattern 11, for example, stainless steel, copper, copper alloy, aluminum, copper-beryllium, phosphor bronze, alloy and the like can be mentioned, with preference given to copper and copper alloy, from aspects of conductivity and rigidity.

A thickness of the wiring pattern 11 is preferably 3-50 μm, and more preferably 5-20 μm. When the thickness of the wiring pattern 11 is less than 3 μm, it is unpreferably susceptible to damage due to a mechanical stress such as bending and the like, local pressure, wear and the like, and when it is greater than 50 μm, wiring at a fine pitch is difficult to achieve, and deformation does not occur easily.

A width of the wiring pattern 11 is preferably 5-100 μm, and a space between adjacent wirings in multiple wiring patterns 11 is preferably as narrow as possible within a range free of inconveniences such as occurrence of unnecessary noise to electrical signals, short circuit due to metal ion migration and the like, and it is generally selected from a range of 5-100 μm.

Generally, a part (normally an end) of the wiring pattern 11 is not covered with the cover insulating layer 12, and is used as a terminal part for an electric connection with other conductor members such as metal wire and the like. Where necessary, the terminal part may be coated with a highly conductive metal such as nickel, gold, solder, tin and the like.

Figure 7:
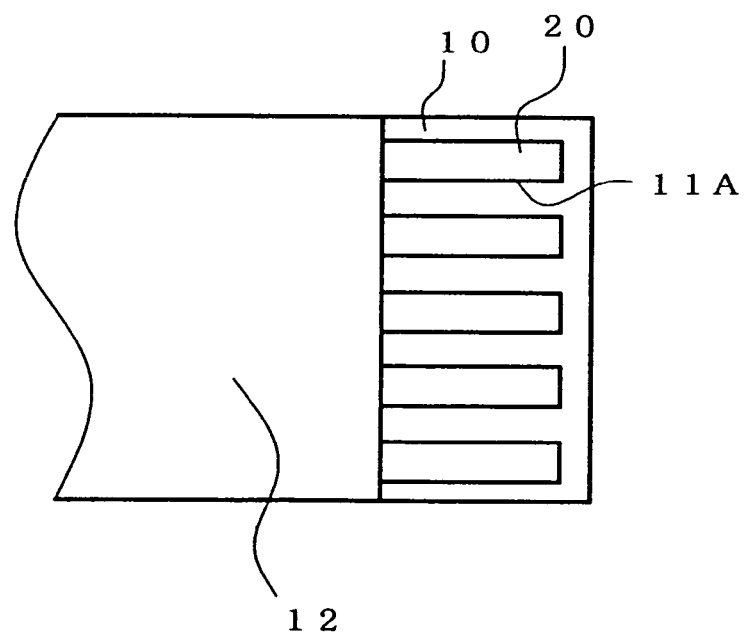
FIG. 7 is a plan view of one embodiment of an arrangement of terminals in the flexible printed circuit board for a catheter of the present invention.
Figure 8:
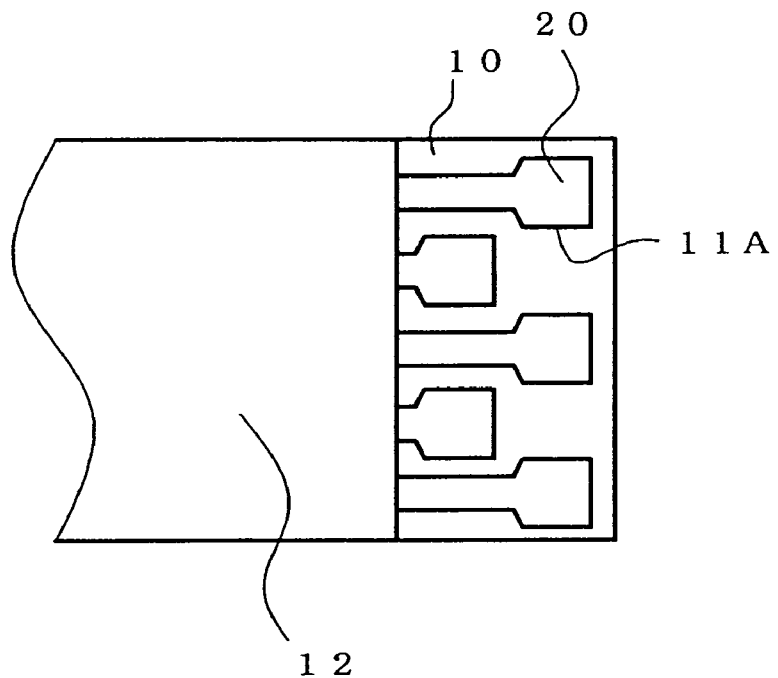
FIG. 8 is a plan view of another embodiment of an arrangement of terminals in the flexible printed circuit board for a catheter of the present invention.

FIGS. 7 and 8 are plan views of the vicinity of an end portion of multiple wiring patterns of the FPC of the present invention. In the FPC of the present invention, end portions 11A of the multiple wiring patterns 11 may, as in the embodiment shown in FIG. 7, align in a single straight line, or as in the embodiment shown in FIG. 8, an end portion on a tip side and an end portion on a posterior end side may be alternately arranged to form a pattern. End portion 11A may be made to have a pattern formed by end portions having different positions alternately arranged as mentioned above, whereby an area of the terminal part (a surface of the end portion) 20 of each wiring pattern can be preferably enlarged and easily connected to a metal wire and the like.

Figure 9:
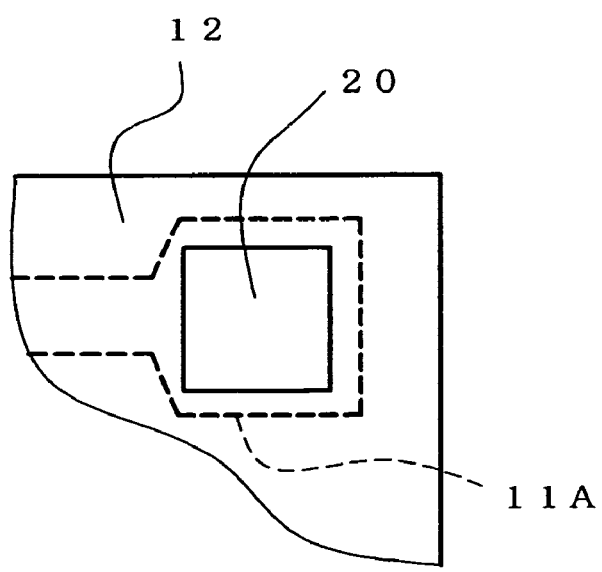
FIG. 9 is a plan view of one embodiment of exposure of a terminal in the flexible printed circuit board for a catheter of the present invention.

In the embodiments shown in FIG. 7 and FIG. 8, the terminal part (the surface of the end portion) 20 of the wiring pattern is entirely exposed to the outside. As show in FIG. 9, a part of the wiring pattern may be formed to appear from an opening of cover insulating layer 12.

A thickness of the cover insulating layer 12 is preferably 2-50 μm. When it is less than 2 μm, dispersion in thickness and partial insulation failure due to bending and wear tend to occur, and when it exceeds 50 μm, flexibility tends to be degraded.

Figure 10A:
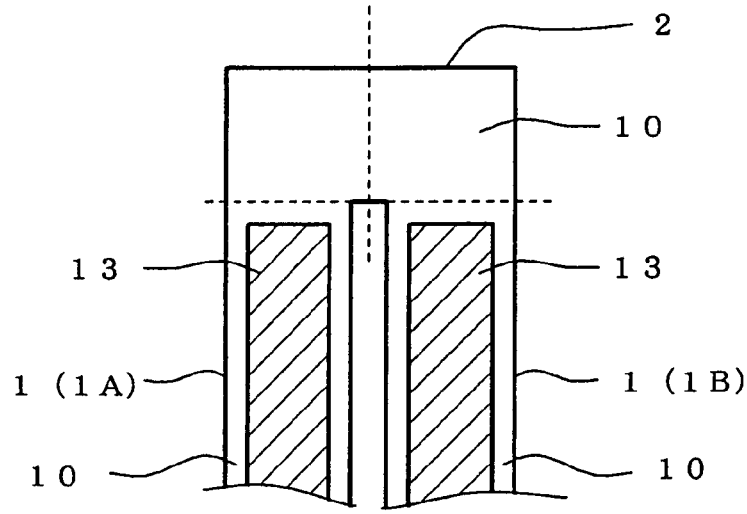
FIGS. 10(a)-10(c) show simplified views of arrangements of metal support plates in the flexible printed circuit board for a catheter of the present invention.
Figure 10B:
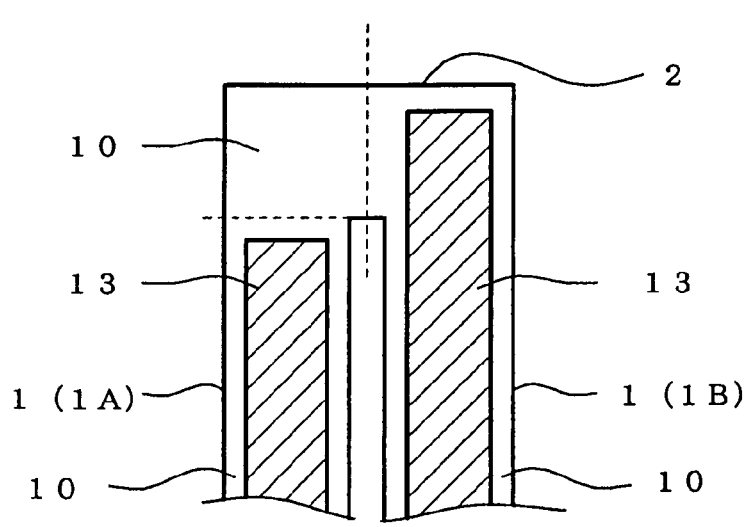
Figure 10C:
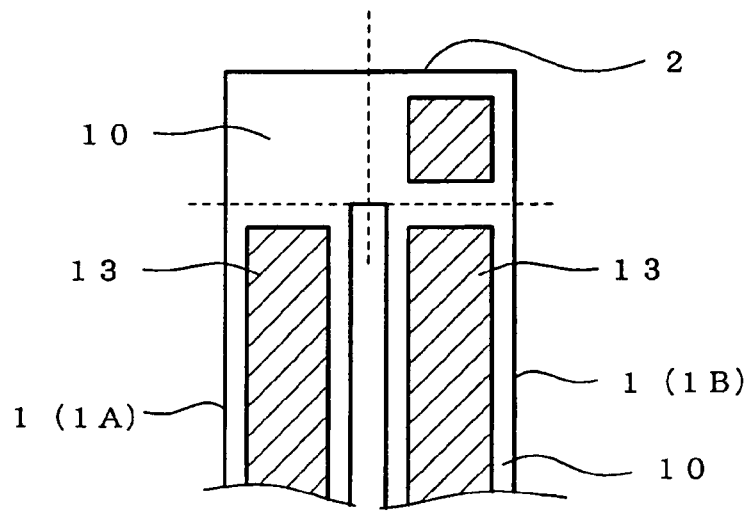

FIGS. 10(a)-10(c) are plan views enlarging a main part of a base insulating layer of another embodiment of the FPC of the present invention, which is on an opposite surface from a surface where a wiring pattern is formed. As shown in these Figures, the FPC of the present invention may have a structure where a metal support plate 13 is laminated on a surface of the base insulating layer 10, which is opposite from the surface where the wiring pattern 11 is formed.

When FPC has such metal support plate 13, insertion of the FPC into a tube is facilitated, since the metal support plate 13 increases rigidity of the FPC as a whole. Moreover, unnecessary bending of a catheter and the like do not occur easily, and the catheter can be easily advanced in a desired direction in a body. As a result, operability of insertion of the catheter into the body is improved.

In the embodiment of FIG. 10(a), a metal support plate 13 is not laminated on a boundary between folding margin 2 and linear part 1, and the folding margin 2. The metal support plate 13 is laminated only on the linear part 1.

This embodiment is preferable for insertability into a tube, since the metal support plate 13 is not layered when the folding margin 2 is double-folded and a thickness of the folding part does not increase. In addition, it is superior in terms of flexibility and can be folded easily.

In the embodiment shown in FIG. 10(b), a metal support plate 13 is not laminated on a boundary between [one (1A) of two linear parts 1 (1A, 1B) to be folded back in a direction opposite by 180 degrees during a folding step] and folding margin 2, and the folding margin 2 (about half area of the folding margin) connected to the boundary. In other words, in the embodiment shown in this embodiment, the metal support plate 13 is laminated on two linear parts 1A, 1B, and the metal support plate 13 laminated on the other (1B) of the two linear parts 1 (1A, 1B) not to be folded back in the direction opposite by 180 degrees during the folding step is extended beyond the boundary between the linear part 1B and the folding margin 2 to cover an about half an area of the folding margin 2.

In this embodiment, FPC is converted to a single linear product by folding back the linear part 1A (linear part connected to the half area of the folding margin 2, which is free of the metal support plate) in the direction opposite by 180 degrees. In this case, when FPC is converted to a single linear product, since the metal support plate 13 is present on the folding part, rigidity of the linear product in its entirety can be enhanced uniformly. Therefore, insertion of the product into a tube is further facilitated, as compared to the FPC in the embodiment of the above-mentioned FIG. 10(a).

In the embodiment of FIG. 10(c), a metal support plate 13 is not laminated on a boundary between a folding margin 2 and two linear parts 1A, 1B connected thereto, and about half an area of the folding margin 2 connected to the boundary with one of the two linear parts 1A, 1B. In other words, in the embodiment of this Figure, the metal support plate 13 is laminated on two linear parts 1A, 1B, and a remaining half of the folding margin 2.

In the FPC of this embodiment, since a metal support plate 13 is not laminated on the boundary between a folding margin 2 and two linear parts 1A, 1B connected thereto, any one of the two linear parts 1A, 1B connected to the folding margin 2 may be folded back in a direction opposite by 180 degrees. Therefore, a folding step for forming a single linear product can be performed rapidly, as compared to the FPC in the embodiment of the above-mentioned FIG. 10(b).

While a metal support plate is absent on the boundary between a folding margin 2 and two linear parts 1A, 1B connected thereto, since the metal support plate 13 is present on the folding margin 2, when FPC is converted to a single linear product, generally rigidity of the linear product in its entirety can be enhanced, which in turn further facilitates insertion of the product into a tube, as compared to the FPC in the embodiment of the above-mentioned FIG. 10(a).

Figure 14:
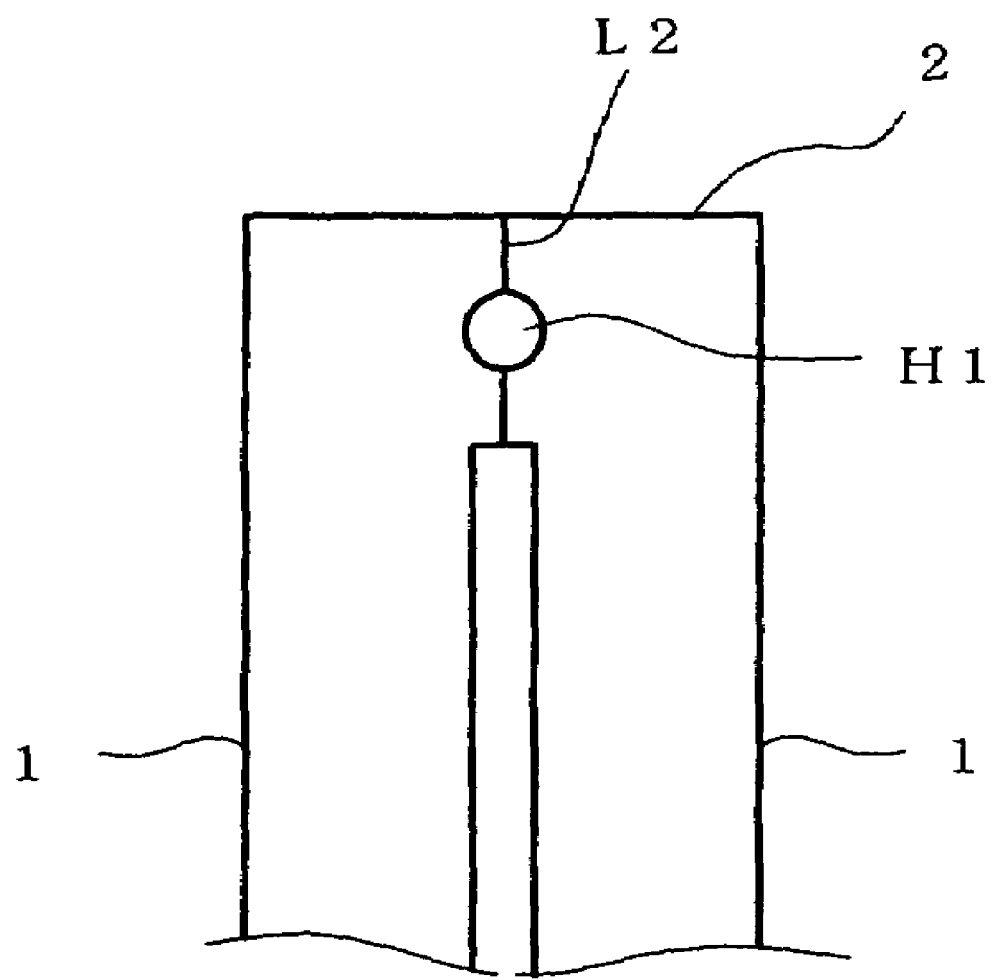
FIG. 14 shows a deformation example of the folding margin of the flexible printed circuit board for a catheter of the present invention.

To facilitate double-folding of the folding margin 2 and to reduce stress applied to FPC during folding, as shown in FIG. 14, a through hole H1 may be formed in a part overlapping with folding line L2 of the folding margin 2. The through hole H1 needs to be formed in a part free of a wiring pattern.

The dotted lines in FIG. 10(a)-(c) are folding (back) lines formed during folding of FPC. A folding line parallel to an axis of a linear part is formed in the boundary between the folding margin 2 and two linear parts 1A, 1B connected thereto at about a center of the folding margin 2. In the wiring circuit board of the present invention, the metal support plate 13 is preferably installed avoiding a part to be a folding line of FPC. As a result, folding of FPC can be completely smooth.

When FPC is a laminate having a metal support plate 13, a width (width in a direction perpendicular to an axis of FPC) of the metal support plate 13 is preferably smaller than a width (width in the direction perpendicular to the axis of FPC) of the base insulating layer 10, and a metal support plate is absent on both ends in a short (width) direction of FPC (direction perpendicular to the axis of FPC).

By this constitution, even when a corner in the short direction of FPC hits an inner wall of a tube during insertion of FPC into the tube, the inner wall of the tube is not injured and FPC can be inserted smoothly. A difference between the width of the metal support plate and the width of the base insulating layer is preferably about 0.02-0.5 mm.

In the present invention, as a material of the metal support plate 13, a single metal element such as stainless steel, steel, nickel, chrome, iron, tin, lead, aluminum and the like, and an alloy of at least two of these metals and the like can be mentioned. Of these, stainless steel is preferable in view of its high elastic modulus.

The elastic modulus of the metal support plate 13 is preferably not less than 50 GPa, and more preferably not less than 100 GPa, in consideration of insertability of a flexible printed circuit board into a tube and operability of a catheter. However, when the elastic modulus is too high, the metal support plate is difficult to bend after insertion into a tube or lacks flexibility. Thus, the elastic modulus is preferably not more than 400 GPa, and more preferably not more than 300 GPa.

As used herein, the "elastic modulus" means tensile elasticity as measured under test conditions of a test piece width 20 mm, distance between chucks 100 mm, and tension rate 50 mm/min.

In addition, a thickness of the metal support plate 13 is generally preferably about 10-200 µm, and more preferably 20-50 µm. When the thickness of the metal support plate 13 is less than 10 µm, an FPC easily develops curls and swelling, which in turn may render insertion of the FPC into a tube difficult. On the other hand, when the metal support plate 13 is thicker than 200 µm, flexibility of an FPC is degraded, which in turn may render insertion of the FPC into a tube difficult.

In the present invention, a total thickness of FPC before folding (including both FPC having a metal support plate 13 and FPC free of a metal support plate 13) is preferably 30-300 µm, and more preferably 40-150 µm. When the total thickness is smaller than 30 µm, mechanical strength becomes insufficient and insertion into a tube becomes difficult or wire breakage easily occurs. When the total thickness is greater than 300 µm, flexibility of a catheter is degraded, and operability during insertion of the catheter into a body is degraded.

Inventive FPC for a catheter is folded at a folding margin set at a predetermined position to form a single linear product (generally a linear product having a total length of not less than 300 mm), and then this single linear FPC is inserted into a tube which is an outer packaging of a catheter.

A folding part (overlap of substrate) formed by folding at folding margin(s) may become unstable because rigidity of FPC tries to restore a shape before folding. To stabilize a shape of the folding part, therefore, two opposite substrate surfaces after folding may be adhered via an adhesive.

Figure 11A:
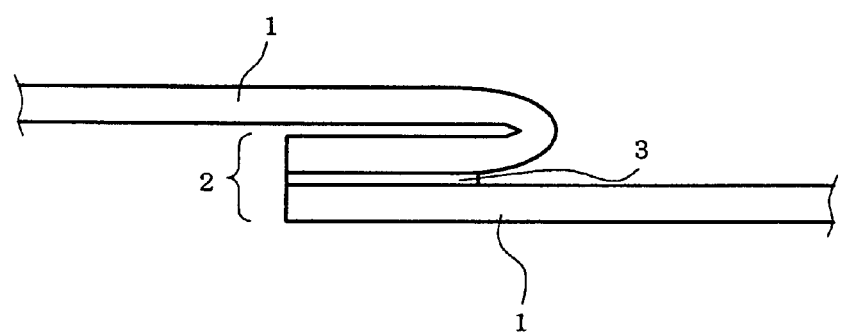
FIGS. 11(a) and 11(b) include simplified side views showing folding part stabilized structures in the flexible printed circuit board for a catheter of the present invention.
Figure 11B:
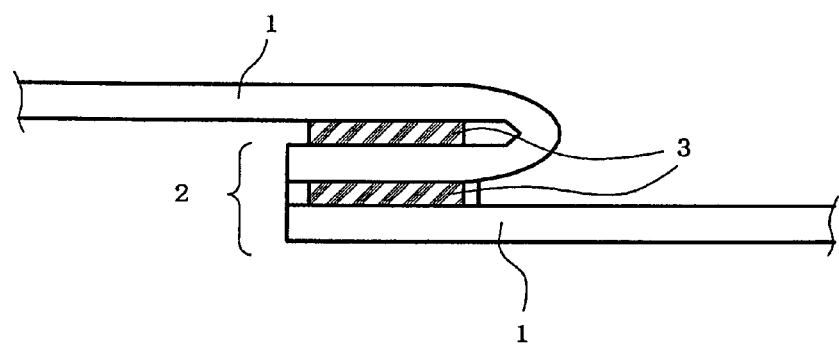

FIGS. 11(*a*), (*b*) show specific examples of such reinforcing (stabilization) structure. FIG. 11(*a*) shows a structure wherein a folding margin 2 is double-folded at about a center thereof, and facing surfaces are adhered via an adhesive layer 3. FIG. 11(*b*) is a structure wherein a folding margin 2 is double-folded at about a center thereof, facing surfaces are adhered via an adhesive layer 3, and a back of a surface opposite to one of these adhered facing surfaces of the folding margin 2 is adhered to a part of linear part 1 folded back in a direction opposite by 180 degrees, which is superimposed thereon, with an adhesive (adhesive layer 3).

As an adhesive to be used for stabilization of the folding part, silicone adhesives, acrylic adhesives, epoxy adhesives and the like can be mentioned.

A thickness of the adhesive layer 3 is preferably 5-50 µm, more preferably 10-30 µm. When the thickness is less than 5 µm, sufficiently high adhesion cannot be achieved easily and when the thickness exceeds 50 µm, a folded part (folding part) may thicken, or a step between the folded part (folding part) and other part (non-folded part) becomes bigger, which unpreferably results in inhibited insertion into a tube and restricted bendability after insertion into the tube.

A production method of the flexible printed circuit board of the present invention is not particularly limited, and the board can be produced by an appropriate combination of known membrane (layer) forming techniques, membrane (layer) patterning techniques, wiring formation techniques and photolithography techniques for printing and the like, conventionally employed for manufacture of flexible printed circuit boards. For example, the method may be combined with a subtractive method, a semi-additive method and the like.

When a base insulating layer 10 and a cover insulating layer 12 are formed in a given pattern, for example, a method using a photosensitive resin (e.g., photosensitive polyimide and the like) (namely, a photosensitive resin (precursor) layer is subjected to exposure, development, heat curing treatment and the like to form an insulating resin layer in a given pattern), and a method comprising subjecting an insulating resin layer to etching by laser or with plasma to form a given pattern and the like, can be mentioned. In view of workability, positioning accuracy and the like, a method using a photosensitive resin is preferable.

The wiring pattern 11 can be formed, for example, by forming a mask pattern by performing photolithography techniques, and forming a deposit film of a metal for wiring by performing metal deposit film forming techniques such as sputtering, plating and the like.

When a flexible printed circuit board having a metal support plate 13 is to be prepared, a flexible printed circuit board having a base insulating layer 10, a wiring pattern 11 and a cover insulating layer 12 laminated in this order is prepared, and the metal support plate 13 may be adhered to the base insulating layer 10 with an adhesive or a base insulating layer 10, a wiring pattern 11 and a cover insulating layer 12 may be laminated in this order on the metal support plate 13.

When a flexible printed circuit board having a metal support plate 13, which is free of a metal support on both ends in a short direction of a plate substrate is to be prepared, a laminate structure having a metal support plate 13 is prepared and the metal support plate 13 is subjected to partial etching.

A catheter in the present invention can be obtained by folding the FPC of the present invention explained above, thereby forming a single linear product by folding at folding margin(s), and inserting this product into a tube.

In other words, the catheter is produced by folding FPC at a folding margin to give a single linear product (step 1), and FPC, which is a single linear product via step 1, is inserted into a tube (step 2).

When a stabilized structure of a single linear FPC having the aforementioned adhesive on the folding parts is to be introduced, the FPC is folded at folding margins to form a stabilized structure and then inserted into a tube.

As explained in the section of BACKGROUND OF THE INVENTION, in general, in a catheter comprising an electronic component in a tube, after insertion of the catheter in a body of a patient, electrical signals generated by an electronic component installed in an anterior end or intermediate part of the tube are processed by a measuring apparatus connected to a posterior end of the tube outside the body of the patient, and the electronic component is controlled by remote with a control device connected to the posterior end of the tube outside the body of the patient.

Therefore, in a catheter using the FPC of the present invention, the FPC to be inserted into the tube has a length of at least from the vicinity of the electronic component in the tube to the posterior end of the tube and, after insertion into the tube, an end portion (terminal part) of the wiring pattern exposed at an end portion on the posterior end side of the tube in a longitudinal direction (axial direction) is electrically connected to an outside measuring apparatus, control device and the like.

The end portion of FPC to be connected to an outside measuring apparatus, control device and the like on the posterior end side of the tube may have a width smaller or larger than an inner diameter of a tube, and it may be contained in the tube or extending from the posterior opening of the tube.

As material of the tube (outer packaging) of the catheter of the present invention, insulating resin materials such as fluororesins (e.g., polytetrafluoroethylene and the like), silicone resin, high density polyethylene resin, polyurethane resin, polyester resin, polyvinyl chloride and the like are used. In consideration of flexibility, heat resistance, chemical resistance, biocompatibility, processability into a tube and the like, fluororesin is preferable.

While a shape of a section (transverse section) perpendicular to the axis of the tube is not particularly limited, a shape free of corners such as a circle, ellipse and the like are preferable (generally circular). Taking a circle as an example, the inner diameter thereof is preferably about 0.2-3.5 mm, and an outer diameter thereof is preferably about 0.3-4 mm. The inner diameter and the outer diameter are preferably determined to make a thickness of the tube 0.05-1.0 mm.

When a tube having a sectional shape other than a circle is used, it is preferable that the tube have a section whose maximum diameter of an inner periphery and maximum diameter of an outer periphery are within preferable numerical ranges of the inner diameter and outer diameter of the above-mentioned circular section.

In the catheter of the present invention, a length (length in the axial direction) of the tube is generally selected from a range of 30-2500 mm.

As an electronic component to be mounted in the tube in the catheter of the present invention, any electronic component conventionally used for electronic component-loaded catheters can be used. Specifically, a heat element, pressure sensor, thermistor for temperature measurement, ultrasonic oscillator, piezoelectric element and the like can be mentioned.

When a catheter mounting a pressure sensor is produced, the pressure sensor (electronic component) is disposed such that a sensitive surface thereof is exposed from a through hole formed in a side wall of a tube.

Figure 12:
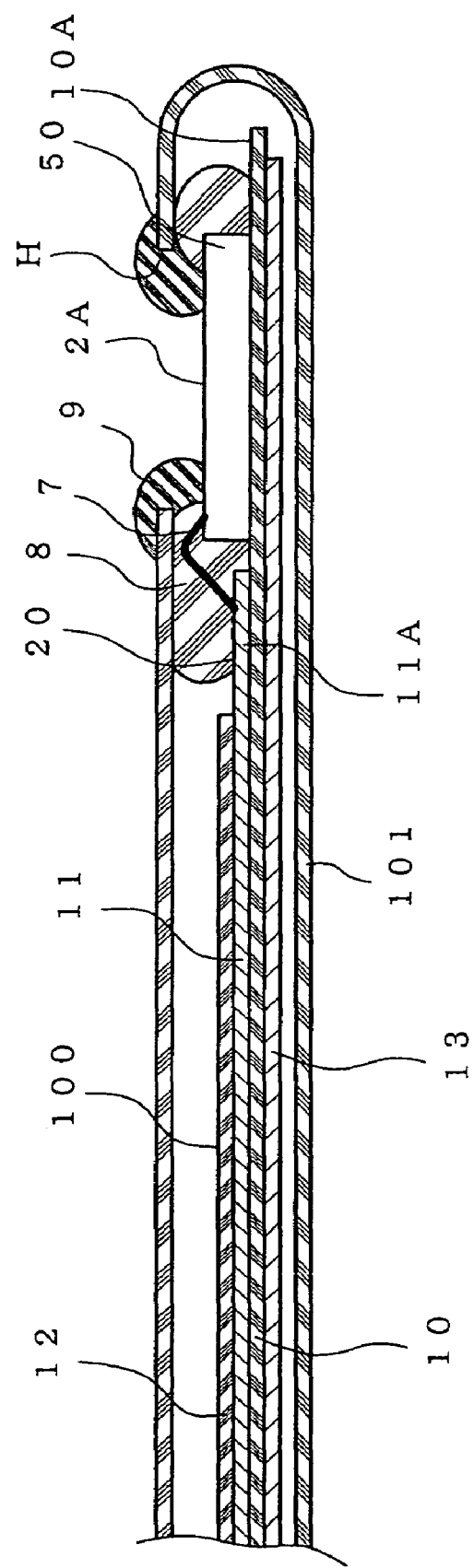
FIG. 12 is a simplified sectional view showing a connection part between an electronic component and a flexible printed circuit board, and the vicinity thereof, in a tube of a catheter in the present invention.

In the catheter of the present invention, a connection (electric connection) between electronic component 50 and FPC 100 is formed in a tube 101, for example, by a method comprising, as shown in FIG. 12, metal welding of a terminal part 20 of a wiring pattern 11 of FPC 100 and a terminal (not shown) of electronic component 50, as in respective bonding of one end and another end of a metal wire 7, a method comprising covering both terminal part 20 formed in a wiring pattern and a terminal of electronic component 50 with a conductive adhesive layer, and the like.

As shown in FIG. 12, connection between the terminal part 20 of a wiring pattern 11 and a terminal of the electronic component 50 is preferably protected by sealing with a resin 8. As the resin 8 for sealing, for example, epoxy resin, fluorine resin, silicone resin and the like can be mentioned.

For fixing an electronic component in a tube 101, as shown in FIG. 12, the electronic component 50 is preferably mounted (fixed) on an area 10A free of wiring patterns which is adjacent to the terminal part 20 formed in the wiring pattern 11 on base insulating layer 10 of the FPC. In this way, the wiring pattern 11 and the electronic component 50 both follow movements of FPC 100, thereby minimizing a load on a connection part therebetween, and connection reliability between the terminal of electronic component 50 and terminal part 20 of wiring pattern 11 is improved.

For mounting (fixing) electronic component 50 on base insulating layer 10, for example, as shown in FIG. 12, resin 8 is used for sealing the connection between terminal part 20 formed on wiring pattern 11 and the terminal of the electronic component 50, wherein the resin 8 is applied to about an entire side surface of the electronic component 50, thereby bridging a surface of the base insulating layer 10 and a periphery of the electronic component 50. By this constitution, mounting (fixing) of electronic component 50 and connection of the terminal of the electronic component 50 to wiring pattern 11 can be simultaneously performed efficiently. The electronic component 50 may be fixed with an adhesive in area 10A near the terminal part 20 formed in the wiring pattern 11 on base insulating layer 10.

As in the catheter 100 of one embodiment shown in FIG. 12, when a catheter having a part of electronic component 50 exposed from through hole H formed in the side wall of tube 101 is produced, it is preferable to apply a sealing resin 9 to cover a periphery of tube walls around the through hole H and an upper surface of the electronic component 50, so as to certainly block an interior of the tube from an exterior thereof.

As the resin 9 for sealing, for example, epoxy resin, fluororesin, silicone resin and the like are used. When a sensitive surface of the electronic component does not need to be exposed to the exterior of the tube, as in a temperature sensor, tube walls may not have a through hole and the electronic component may be enclosed in the tube. In this case, a resin for sealing is not necessary.

EXAMPLES

The present invention is explained in more detail in the following by referring to Examples, which are not to be construed as limitative.

Example 1

Figure 13:
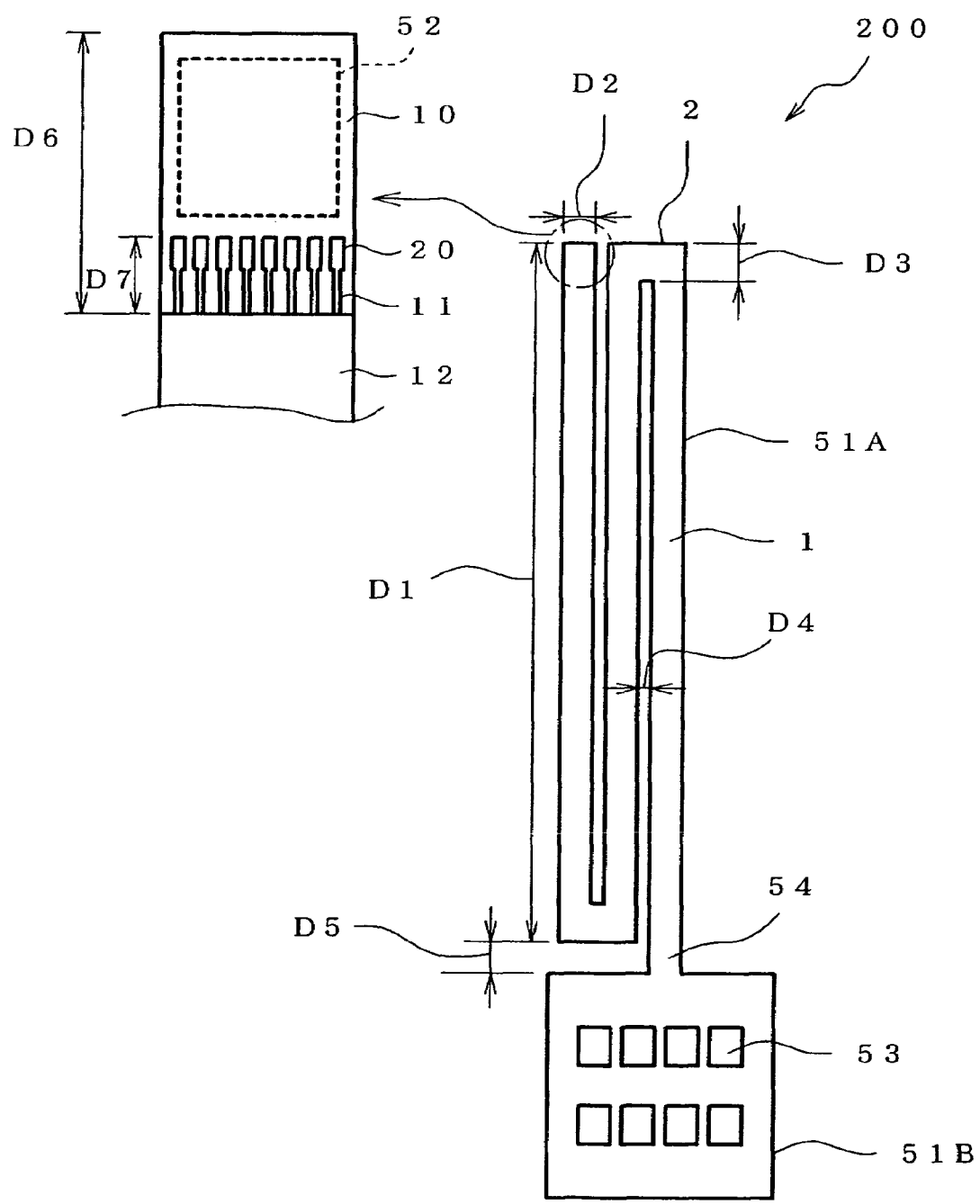
FIG. 13 is a simplified plan view of the flexible printed circuit board for a catheter prepared in Example 1.

In this example, FPC 200 shown in FIG. 13, which comprises eight wiring patterns formed on a stainless steel substrate by a semi-additive method was produced.

This FPC 200 has three linear parts 1 and folding margins 2 having a rectangular pattern to connect the linear parts, and has a band-like meandering pattern as a whole. An electronic component mounting part 52 is partitioned in an end portion on one side in an axial direction, eight wiring patterns 11 are disposed with each end set close to the electronic component mounting part 52, and terminals 20 for connection with an electronic component are formed on the end. An area containing the electronic component mounting part 52 and terminals 20 of respective wiring patterns 11 is exposed without being covered with a cover insulating layer 12. In an end portion on another side in the axial direction is partitioned a substrate part 51B having about a square plan shape for connection with an external device. The substrate part 51B contains eight terminals 53 for connection with the external device, which are exposed from openings formed in a cover insulating layer. The substrate part 51B for connection protrudes outside from a posterior end of a tube when FPC 200 is inserted into the tube. A size of each part is as shown below.

- length (D1) of linear part 1: 210 mm
- width (D2) of linear part 1: 1 mm
- clearance (D4) between adjacent linear parts: 50 µm
- width (D3) of folding margin (rectangle pattern part) 2: 2 mm
- planar size of substrate part 51B for connection with external device: 8 mm×8 mm
- length (D5) of drawing part 54 from an end of linear part 1 to substrate part 51B for connection: 0.5 mm
- distance (D6) from an end edge of FPC on a side where electronic component mounting part 52 is partitioned to an end edge of cover insulating layer 12: 2 mm
- length (D7) of exposure of wiring pattern 11 from end edge of cover insulating layer 12: 500 µm
- planar size of terminal 20: 80 µm×160 µm
- planar size of terminal 53: 1.5 mm×2 mm FPC 200 having the above-mentioned structure and size was prepared by the following steps.

First of all, a photosensitive polyimide precursor was applied to a stainless substrate (SUS304) (length: total length 250 mm, width: 250 mm, thickness: 20 µm, elastic modulus: 205 GPa) as a metal support plate, which was then subjected to light exposure, development and heating to provide a 10 µm thick base insulating layer made of polyimide, which has a predetermined shape.

Then, by continuous sputtering, a metal thin film (chrome thin film (thickness: 100 nm)/copper thin film (thickness: 100 nm)) was deposited on a surface of a base insulating layer and a metal support plate. A plating mask having an inverse pattern to a wiring pattern to be formed was prepared by photoresist (i.e., pattern having the same opening areas as the wiring pattern to be formed).

Then, a copper layer (thickness: 10 µm) was grown on a part free of a resist (opening of a mask for plating) by electrolytic copper plating, and eight wiring patterns running parallel to each other along a longitudinal direction of the base insulating layer were formed, after which the mask for plating (resist) was peeled off and an exposed metal thin film was removed by etching.

A width of this copper wiring pattern was 30 µm, and a space between adjacent patterns was 30 µm.

Then, in the same manner as in the base insulating layer, coating with a photosensitive polyimide precursor, exposure, development and heating were successively performed, a cover insulating layer (thickness: 5 µm) made from polyimide, which had a given pattern including an opening (part free of polyimide layer formation) on an end part that became a terminal part of the copper wiring pattern was formed, and a nickel (thickness: µm)/gold (thickness: 0.2 µm) plating was applied to an end part of the copper wiring pattern, which was exposed from an opening of a cover insulating layer, to form a terminal part.

Then, a photoresist pattern was formed on a surface opposite from a surface where a base insulating layer of the metal support plate (stainless steel substrate) was formed, and, using the photoresist pattern as a mask, both ends of the metal support plate (stainless steel substrate) in a width direction were removed by etching. By removing the photoresist pattern, both ends of the base insulating layer in the width direction were protruded by 50 µm from both ends (end part) of the metal support plate (stainless steel substrate) in the width direction. In this case, the metal support plate (stainless steel substrate) was removed from a half area of a folding margin (to be connected to one of two linear parts) and a boundary between this area and one of the linear parts, so that the base insulating layer can be exposed. As a result, a plan view from a metal support plate side was as shown in FIG. 10(b).

In this way, an FPC 200 of a size that fits in a square area (250 mm×250 mm) of FIG. 13 in a plan view was prepared.

Main substrate part 51A (to be inserted into a tube) is connected with substrate part 51B (8 mm×8 mm) for connection with an external device.

The above-mentioned main substrate part 51A consists of three linear parts and two rectangular patterns connected to the three linear parts, and is a meander band. Each rectangular pattern is a folding margin.

Each of the above-mentioned three linear parts has a length (D1) of 210 mm and a width (D2) of 1 mm, and the three parts are configured in parallel with each other with a 50 µm clearance (D4).

The above-mentioned rectangular pattern (folding margin) has a width (D3) of 2 mm in a direction perpendicular to its axis.

This FPC 200 was folded at two folding margins to provide a single linear product having a total length (=total length of the main substrate part 51A) of 622 mm, and an epoxy adhesive was fed at a spot and cured between facing substrate surfaces in the folding part. A thickness of the adhesive layer was set to 20 µm.

A fluorine resin tube having an inner diameter of 1.2 mm, an outer diameter of 1.5 mm, and a length (length in an axial direction) of 600 mm was prepared and through holes (size of hole: 2 mm×0.4 mm (quadrangle)) were formed in a side wall at 5 mm away from one end portion in the axial direction of the tube.

Then, a pressure sensor (whole size (length=3 mm, width=0.5 mm, thickness=250 µm), terminal size: 80 µm×80 µm (quadrangle)) was placed on an electronic component mounting part 52 partitioned in an end portion of the base insulating layer of FPC 200 converted to the aforementioned single linear product. A terminal of the pressure sensor and a terminal 20 formed in an end of the wiring pattern 11 were wire bonded with a gold wire to electrically connect them. Thereafter, the FPC 200 was inserted from another end portion (posterior end side) of the aforementioned fluororesin tube in the axial direction. Then, via a through hole formed in a tube side wall, this gold wire connection between the terminal of the pressure sensor and the terminal formed in the end of the wiring pattern was sealed with an epoxy resin. A sealing silicone resin was further applied to an area surrounding the through hole of the tube and a clearance of the pressure sensor to provide a catheter with a pressure sensor.

During production of the catheter, the FPC could be inserted smoothly into the tube. This obtained catheter with a pressure sensor contained eight wiring patterns but showed fine flexibility, and could be inserted into a body of a test subject (examinee) with good operability. The test subject did not complain of pain during insertion of the catheter.

This application is based on a patent application No. 2005-121493 filed in Japan, the contents of which are hereby incorporated by reference.

What is claimed is:

1. A flexible printed circuit board for a catheter, comprising:
   a substrate including
      (i) a base insulating layer,
      (ii) a wiring pattern on one surface of said base insulating layer, and
      (iii) at least two support plates on a surface of said base insulating layer that is opposite to said one surface,
   wherein said substrate has a form of a single non-linear band-like pattern including two substantially parallel linear parts and a folding margin interconnecting said two linear parts at longitudinal ends of said two linear parts, with said substrate being constructed and arranged to be turned into a single substantially linear product by folding said folding margin about a first folding line that is parallel to longitudinal axes of said two linear parts, and at said folding margin, folding one of said two linear parts by 180 degrees about a second folding line which is transverse to said first folding line, and
   wherein said at least two support plates comprise one of
      (a) a first support plate laminated only on one of said two linear parts, and a second support plate laminated only on the other of said two linear parts,
      (b) a first support plate laminated on one of said two linear parts, and a second support plate laminated on the other of said two linear parts and a portion of said folding margin adjacent the other of said two linear parts, and
      (c) a first support plate laminated on one of said two linear parts, a second support plate laminated on the other of said two linear parts, and a third support plate laminated on a portion of said folding margin adjacent the other of said two linear parts, with the proviso that said second support plate does not extend onto the portion of said folding margin and said third support plate does not extend onto the other of said two linear parts.

2. The flexible printed circuit board according to claim 1, wherein
   said at least two support plates comprise at least two metal support plates.

3. The flexible printed circuit board according to claim 2, wherein
   said single linear product has a total length of not less than 300 mm.

4. The flexible printed circuit board according to claim 2, wherein
   said substrate has a form of a single non-linear meandering band-like pattern including multiple linear parts and multiple folding margins interconnecting said multiple linear parts at longitudinal ends thereof.

5. The flexible printed circuit board according to claim 4, wherein
   said single linear product has a total length of not less than 300 mm.

6. The flexible printed circuit board according to claim 2, wherein
   a size of said substrate as a whole, before being turned into said single linear product, is within a 250 mm×250 mm square area.

7. The flexible printed circuit board according to claim 2, wherein
   said single linear product includes opposing surfaces at said folding margin, with said opposing surfaces being adhered to one another via an adhesive layer.

8. A catheter comprising:
   the flexible printed circuit board of claim 2, as said single linear product, within a tube.

9. A method of producing a catheter, comprising:
   turning said substrate of the flexible printed circuit board of claim 2 into said single linear product by folding said folding margin about said first folding line, and at said folding margin, folding one of said two linear parts by 180 degrees about said second folding line; and
   inserting said flexible printed circuit board of claim 2, as said single linear product, into a tube.

10. The method according to claim 9, further comprising:
    after turning said substrate into said single linear product, and before inserting said flexible printed circuit board into said tube, adhering, via an adhesive layer, two opposing surfaces of said single linear product at said folding margin.

11. The flexible printed circuit board according to claim 1, wherein
    said single linear product has a total length of not less than 300 mm.

12. The flexible printed circuit board according to claim 1, wherein
    said substrate has a form of a single non-linear meandering band-like pattern including multiple linear parts and multiple folding margins interconnecting said multiple linear parts at longitudinal ends thereof.

13. The flexible printed circuit board according to claim 12, wherein
    said single linear product has a total length of not less than 300 mm.

14. The flexible printed circuit board according to claim 1, wherein
    a size of said substrate as a whole, before being turned into said single linear product, is within a 250 mm×250 mm square area.

15. The flexible printed circuit board according to claim 1, wherein
    said single linear product includes opposing surfaces at said folding margin, with said opposing surfaces being adhered to one another via an adhesive layer.

16. A catheter comprising:
    the flexible printed circuit board of claim 1, as said single linear product, within a tube.

17. A method of producing a catheter, comprising:
    turning said substrate of the flexible printed circuit board of claim 1 into said single linear product by folding said folding margin about said first folding line, and at said folding margin, folding one of said two linear parts by 180 degrees about said second folding line; and inserting said flexible printed circuit board of claim 1, as said single linear product, into a tube.

18. The method according to claim 17, further comprising:
- after turning said substrate into said single linear product, and before inserting said flexible printed circuit board into said tube, adhering, via an adhesive layer, two opposing surfaces of said single linear product at said folding margin.

19. A method of producing a catheter, comprising:
providing a substrate including
  (i) a base insulating layer, and
  (ii) a wiring pattern on one surface of said base insulating layer,
wherein said substrate has a form of a single non-linear meandering band-like pattern including multiple linear parts and folding margins interconnecting said multiple linear parts at longitudinal ends of said multiple linear parts, with each one of said folding margins interconnecting two adjacent ones of said multiple linear parts;

turning said substrate into a single substantially linear product by folding said each one of said folding margins about a first folding line that is parallel to longitudinal axes of a corresponding two adjacent ones of said multiple linear parts, and at said each one of said folding margins, folding one of said corresponding two adjacent ones of said multiple linear parts by 180 degrees about a second folding line that is transverse to said first folding line; and inserting said single substantially linear product into a tube.

* * * * *